United States Patent [19]

Griffith et al.

[11] Patent Number: 5,292,927

[45] Date of Patent: Mar. 8, 1994

[54] FLUORINATED RESINS WITH LOW DIELECTRIC CONSTANT

[75] Inventors: James R. Griffith, Lanham; Henry S. W. Hu, Derwood, both of Md.

[73] Assignee: The United States of America as represented by the Secretary of the Navy, Washington, D.C.

[21] Appl. No.: 841,944

[22] Filed: Feb. 26, 1992

[51] Int. Cl.$^5$ .................... C07C 69/52; C07C 41/00
[52] U.S. Cl. .................................. 560/221; 568/662; 526/242; 526/245; 526/247
[58] Field of Search ........................................ 560/221

[56] References Cited

U.S. PATENT DOCUMENTS 4,633,023 12/1986 Griffith et al. .................... 568/662

Primary Examiner—José G. Dees
Assistant Examiner—Dwayne C. Jones
Attorney, Agent, or Firm—Thomas E. McDonnell; George A. Kap

[57] ABSTRACT

A highly fluorinated benzene compound is reacted with acryloyl chloride to yield a fluorinated liquid product which is used to impregnate a reinforcing structure. Upon impregnation, the liquid material is polymerized at about 55°C. to produce a reinforced polymeric structure, which can be a circuit board. The polymer has dielectric constant of about 2.1, which is very low compared to the polymers used presently.

4 Claims, No Drawings

FLUORINATED RESINS WITH LOW DIELECTRIC CONSTANT

BACKGROUND OF INVENTION

Dielectric constant is defined as a measure of the ability of a dielectric to store an electric charge. A dielectric is a nonconducting substance or an insulator. Dielectric constant is directly proportional to capacitance of a material, which means that capacitance is reduced if dielectric constant of a material is reduced. For high frequency high-speed digital circuits, capacitance of substrates and coatings are critical to reliable functioning of the circuits. Present computer operations are limited by the coupling capacitance between circuit paths and integrated circuits on multilayer boards. The computing speed between integrated circuits is reduced by this capacitance and the power required to operate them is increased.

With recent trends toward microminiaturization and utilization of very thin conductor lines, close spacings, and very thin insulation of 5 mils or less, greater demands are being placed on the insulating layer. Insulating materials must possess very low dielectric constants and at the same time must retain other required engineering and manufacturing properties. For high frequency linear circuits, such as those used in radar assemblies, the dielectric constant of insulators again becomes important, especially since it may vary with changes in frequency.

Poly(tetrafluoroethylene), which is a solid at room temperature and is known as Teflon ® dielectric material, has dielectric constant in the range of 2.00–2.08 and tetrafluoroethylene which is a gas at room temperature, has dielectric constant in the range of 1.89–1.93. Poly(tetrafluoroethylene) is completely chemically inert, has excellent electrical properties, has outstanding stability, and retains mechanical properties at high temperatures. The problem with poly(tetrafluoroethylene) is that it is not processable. Teflon ®AF dielectric material, a commercial material, is believed to be a terpolymer of tetrafluoroethylene, perfluoropropylene and a derivative of hexafluoracetone. Teflon AF material is believed to have a dielectric constant of 1.92 and although it is more processable that poly(tetrafluoroethylene), it still lacks adequate processability.

U.S. Pat. No. 4,452,998 and U.S. Pat. No. 4,356,296 disclose fluorinated diacrylic esters which are prepared by reacting a substituted benzene with acryloyl chloride in a highly fluorinated solvent in the presence of a tertiary amine, such as triethyl amine, or another acid acceptor, at 5° to 20° C. The monomer is purified and can then be polymerized. The fluorinated diacrylic esters of this patent are disclosed to be useful particularly in dental and biomediacal applications.

The conventional material for ordinary printed circuit boards is epoxy resin impregnated glass fiber laminates although paper laminates may still be used in less arduous environments, such as in hi-fi equipment and domestic appliances. The use of flame retardant materials has become almost universal use to danger of fire in electronic and electrical equipment. The metal foils, preferably copper, applied to the non-conducting layers of a circuit board are usually 25 to 75 microns in thickness although some are 5 to 12 microns.

Multilayer printed circuit boards have been made of organic polymers, such as glass epoxy resins, since such materials have a low dielectric constant of about 4, however, it is impossible to directly mount integrated circuit chips in such boards because of their poor thermal resistance and inadequate physical properties to produce many insulated internal layers. This brought forth alumina ceramic circuit boards but problems were encountered due to the high dielectric constants of 9 to 10. With the advent of super computers, there is a tendency to use pulses with high frequency. At high frequency, the delay of propagation of signals is increased due to the relatively high dielectric constant of the insulating material. Also, there is an increase in electrostatic capacitance between adjacent wiring conductors which results in attenuation of signals as well as decrease in circuit impedance, if high dielectric constant insulator materials are used for insulators.

U.S. Pat. No. 4,452,998 and U.S. Pat. No. 4,356,296 to Griffith et al. disclose fluorinated diacrylic esters useful in dental and in biomedical applications as well as in the traditional acrylic applications such as coating, casting, encapsulanting, caulking, and the like.

SUMMARY OF INVENTION

An object of this invention is the processable fluorinated aromatic acrylates which have a low dielectric constant.

Another object of this invention is the fluorinated aromatic ether acrylates containing at least 14 fluorine atoms which are processable at ambient temperature and which can be cured to a solid at elevated temperature in the presence of an effective amount of a curing catalyst.

Another object of this invention is the use of processable monomeric fluorinated aromatic acrylates in liquid state to form electronic parts which require low dielectric constant and then curing the liquid acrylates at an elevated temperature to a solid state.

These and other objects are accomplished by processable liquid monomeric fluorinated aromatic acrylate which are liquid at ambient temperature and which are cured to a solid state at elevated temperature.

DETAILED DESCRIPTION OF THE INVENTION

This invention pertains to processable monomeric fluorinated aromatic acrylates having low dielectric constants which are liquid at ambient or room temperature and which can be cured to a solid state at elevated temperature. This invention also pertains to electronic articles made from the processable monomers of the fluorinated aromatic acrylates which are cured to solid form and which have low dielectric constants.

The monomers suitable herein are liquids at room temperature and can polymerize to solids at elevated temperatures. Viscosity of these monomers varies from thin to syrupy liquids which enables their use to impregnate reinforcing materials, such as fiber glass scrim, used in making wiring boards or circuit boards or other electronic components used in electrical or electronic applications. To enable use of the highly fluorinated monomers disclosed herein where impregnation or another processing step or steps are involved, the monomers must be in a liquid form, having viscosity below about 10,000 centistokes at 25° C.

Since the monomers are liquids at room temperature or are low melting solids, they are easily processable and can be used to impregnate reinforcing material or be used in other ways to form solid plastic components on polymerization. The liquid monomers can be cured to solid state by incorporating therein a curing catalyst and heating the monomers below the decomposition temperature thereof. In the presence of an effective amount of a curing catalyst, the monomers can be polymerized by heating to a temperature of about 50° to 100° C.

Suitable monomers herein are liquids at room temperature or solids that melt at low temperatures and include fluorinated aromatic compounds having attached to the aromatic moiety at least one but preferably at least two or three of the following groups:

$$R^1-R^2-R^3-$$

and one or more groups, preferably one, having the following structure:

$$R^4-O-(CX_2)_n-$$

where $R^1$ is an unsaturated radical containing 2 to 18 carbon atoms, preferably a monounsaturated hydrocarbon radical of two to six carbon atoms, more preferably selected from acrylic, allylic, halogenated vinyl, vinyl ether, allyl ether, and mixtures thereof, particularly acrylic and methacrylic groups; $R^2$ is oxygen, nitrogen or sulfur, preferably oxygen; $R^3$ is a fluorinated hydrocarbon radical, preferably perfluorinated saturated hydrocarbon radical of 1 to 8, more preferably 2 to 6 carbon atoms; $R^4$ is a hydrocarbon group of 1 to 18 carbon atoms, preferably a fluorinated or perfluorinated group of 2 to 6 carbon atoms; n is 0 to 18, preferably 2 to 6; and X is hydrogen or a halogen, especially fluorine, provided that each carbon to which an X is attached has at least two, preferably three, fluorine atoms attached thereto. In a more preferred embodiment, the fluorinated aromatic compounds have the following structural formulas I and II:

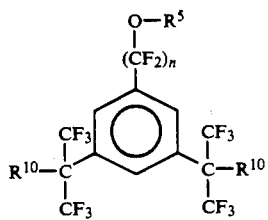

I

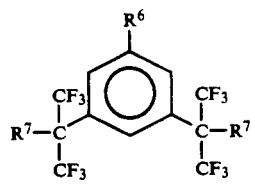

II where n is 0 to 18, preferably 2 to 6; each $R^{10}$ and $R^7$ is individually selected from unsaturated groups of 2 to 18 carbon atoms containing zero to two oxygen atoms, especially 2 to 6 carbons atoms and one to two oxygen atoms, however, in a preferred embodiment, each $R^{10}$ and $R^7$ is individually selected from acrylate, methacrylate, vinyl ether, allyl ether and fluorinated vinyl groups; $R^5$ is selected from hydrogen and hydrocarbon groups of 1 to 18, especially fluorinated hydrocarbon groups of 2 to 6 carbon atoms; and $R^6$ is selected from hydrogen and hydrocarbon groups of 1 to 18 carbon atoms, especially fluorinated hydrocarbon groups of 2 to 6 carbon atoms, however, in a preferred embodiment, $R^6$ is selected from $CF_3$ and $C_2F_5$ groups. In the compounds defined by formula I, both of the $R^{10}$ groups are unsaturated of 2 to 6 carbon atoms with one to two oxygen atoms therein and preferably, both of the $R^{10}$ groups are the same. In the compounds defined by formula II, the $R^7$ groups are unsaturated of 2 to 6 carbon atoms and preferably, both of the $R^7$ groups are the same. In the most preferred embodiment, $R^{10}$ and $R^7$ groups are individually selected from unsubstituted acrylate and unsubstituted methacrylate groups, and $R^5$ is heptafluoroisopropyl group.

The compounds defined by formula I are also referred to herein as fluorinated phenyl hexafluoropropyl ethers, with the hexafluoropropyl groups on the 1 and 3 carbon atoms of the benzene ring and the ether group connected between the $-(CF_2)_n-$ and the $R^5$ groups. The compounds defined by formula II are also referred to herein as fluorinated phenyl hexafluoropropyl compounds, with the hexafluoropropyl groups on the 1 and 3 carbon atoms of the benzene ring but being devoid of the ether group. Collectively, compounds defined by formulas I and II and others which are defined herein are also referred to herein as fluorinated aromatic compounds.

It should be noted that the fluorine atoms on compounds of formula I and II are not on the aromatic structure but on substituents thereon. Putting fluorine atoms on the aromatic ring would render such a compound unstable.

The fluorinated phenyl hexafluoropropyl ethers of formula I and the fluorinated phenyl hexafluoropropyl compounds of formula II have low dielectric constants of less than 2.5 preferably in the range of 1.8 to 2.4, especially 2.0 to 2.3. Due to their low dielectric constants, these compounds are especially suited for electronic applications, such as circuit boards. Dielectric constants of these materials can be further lowered by known means such as by incorporating air bubbles in the materials or by mixing glass therewith. A difference of a couple of hundredths in the dielectric constant value is very important when one is at the low extremes thereof.

The compounds disclosed herein can be prepared by reacting a highly fluorinated monomer with acryloyl chloride in the presence of an acid acceptor, all in a highly fluorinated solvent such as trifluorotrichloroethane, tetrafluoroethane, and tetrafluoropropane. The fluorinated monomer can be prepared by a known multistep route reported by Griffith and O'Rear in Polymer Material Science Engineering, Vol. 53, pp. 766-769(1985) and in the 1981 book entitled "Biomedical And Dental Applications Of Polymers" by Gebelein and Koblitz. The solvent should contain at least 50% substituted fluorine. The preferred acid acceptor is triethylamine. Acryloyl chloride and the acid acceptor should be used in a slight stoichiometric excess. Amount of the solvent should be at least sufficient to dissolve the reactants but should not be used in an amount more than 50% excess. The reaction temperature is about 0° to 30° C., preferably 5° to 20° C.

Certain products of reaction can precipitate out and can be removed by a conventional way, as by filtering. Removal of solid products of reaction facilities purification of the monomer.

The monomer is purified by the method comprising dissolving the crude monomer containing minor amounts of unreacted reactant alcohol and monoester in a solvent such as ether or Freon ® 113 solvent. The resulting solution is clarified, preferably with decolorizing carbon, and then percolated through activated alumina.

The product ester can be easily and quickly polymerized by a free radical catalyst or by u.v. radiation. Polymerization temperature of these monomers is above the melting point of the fluorinated aromatic compounds in the range of about 20° to 100° C., preferably 50° to 80° C., and especially above 55° C. Polymerization should be conducted in an inert atmosphere to avoid tacky surfaces. It is believed that if polymerization is carried out in presence of oxygen, oxygen inhibition takes place at the surface with the resulting tacky surfaces. An effective amount of a polymerization catalyst is also used. The effective amount is generally less than 5% by weight of the monomer, preferably 0.1 to 2%. Polymerization with benzoyl peroxide free radical catalyst should be carried out at about 80° C.; with azobisisobutyronitirle it should be at about 50°-55° C.; and with other catalysts, other temperatures can be used. Free radical polymerization is well known in the art.

These monomers can also be polymerized by heating the monomers above their melting points. The duration of such polymerization is up to 24 hours, however, the monomers can be polymerized solely by heat in 0.1 hours to 4 hours.

The resulting polymers are generally of infinite molecular weight, making a precise molecular weight determination impossible. This is true of the fluorinated aromatic compounds disclosed herein which can have three unsaturated groups on the aromatic moiety which polymerize to form a solid thermosetting polymer. If the fluorinated aromatic compounds contain two or more unsaturated groups through which polymerization takes place, the resulting polymers are solid, crosslinked thermosetting polymers which can be used in the manufacture of the circuit boards or other electronic components since such polymers can withstand operating temperatures in excess of 150° C. The fluorinated aromatic compounds having only one unsaturated group are expected to be polymerized to linear thermoplastic polymers and such polymers are not expected to be used alone in circuit board manufacture. It is contemplated that compounds having only one unsaturated group would be used in a mixture with compounds having two or more unsaturated groups since a compound containing two or three unsaturated groups would be expected to polymerize to a crosslinked, solid, non-linear thermosetting polymer. The fluorinated aromatic compounds which have one unsaturated group can be used in a mixture with the fluorinated aromatic compounds which have two or three unsaturated groups which mixture polymerizes to a solid polymer which can withstand the high temperature operating temperature which the electronic components are exposed to.

As already noted, the fluorinated aromatic compounds disclosed herein are liquids at ambient temperature or temperatures up to the boiling temperature of water, i.e. 100° C., have low dielectric constants in monomer and polymer forms, easily polymerize to solids, and can withstand temperatures in excess of 200° C. These properties render the herein-disclosed monomers especially useful in the manufacture of electronic components, especially circuit or wiring boards, which are used in electronic equipment such as communication equipment, information generating equipment, diagnostic equipment, and other electronic equipment.

The procedure for making circuit boards using a compound disclosed herein generally involves the steps of applying one of the compounds in liquid form to a reinforcement material, curing the liquid compound to a solid state to an article comprising the reinforcing material and the solid compound in polymer form, and applying a conducting material onto the article. In a preferred embodiment, a glass cloth is impregnated with the compound or a mixture thereof in liquid form by means of a wet or prepreg process. A mixture of the fluorinated aromatic compounds can be used in place of only one. The compound can be cured to the final polymer stage or partly to the prepolymer stage and later at convenient time, the prepolymer can be further cured to the final polymer stage, whether thermoplastic or thermosetting, although thermosetting is preferred. At the prepolymer stage, the compound is in the oligomer form. Oligomer herein is considered to be a polymer since it is composed of more than two repeating units of the compound. The reinforcing material can be in the form of fibers, whiskers, or particles. Glass fibers in woven form are preferred.

More specifically, a printed circuit board can be prepared by impregnating a reinforcing material with a fluorinated aromatic compound in liquid form or mixing the compound with a reinforcing material and curing the compound to a solid polymeric form. AT this stage the compound can be cured to a solid prepolymer state or to the final solid polymer state. If the compound is cured to a prepolymer state, it can later be cured to the final polymer state at a convenient time in the manufacture procedure. When used in conjunction with the reinforcing material, the compound can be heated above room temperature and below about 100° C. to render it liquid. In a preferred embodiment, a glass cloth is impregnated with the compound at about 75° C. The main concern here is to keep all components in solution in absence of a solvent. The compounds are non-conductive meaning that they are substantially non-conducting to electric current and have, in monomer and in polymer forms, dielectric constant below about 2.5, particularly 1.8 to 2.3. In some applications, the reinforcing material is not used.

Curing of the fluorinated aromatic compounds can be carried out by heat in presence of an effective amount of a free radical initiator or by radiation to the prepolymer or to the final polymer stage. If curing is accomplished by radiation, the curing step can be accomplished by exposing the compounds to ultraviolet radiation, infrared radiation, gamma radiation, and the like forms of radiation, with ultraviolet radiation being preferred.

While planarity of the non-conductive layer formed from polymerized fluorinated aromatic compound is not critical, a flat layer of substantially uniform thickness is preferred. Thickness of the non-conducting layer can vary widely and is not critical although thickness thereof should be at least as thick as the conducting circuit patterns that are to be embedded therein. In general, thickness of this layer should be at least one micron and in a preferred embodiment, this thickness should be in the range of 5 to 50 microns, especially 15 to 30 microns, in the manufacture of multilayer printed circuit boards.

A metal surface is secured to the non-conducting layer selected from copper, nickel, chromium, palladium, platinum, silver aluminum or the like which is conducting to electricity. Preferred metal surface is copper. The metal surface can be in the form of foil, sputtered metal, or a printed circuit applied to the non-conducting layer as a copper paint, for instance. If the conducting surface is a foil or is applied by sputtering a continuous metal film on the non-conducting layer, a circuit is developed in a known way so that the desired electrical path is effected thereby. Many of such non-conductive layers with printed circuits can be combined to form a multi-layer circuit board. Normally, a printed layout of the wiring appears on one side whereas the component side appears on the opposite side of the circuit board. Manufacturing of circuit or wiring boards is well known and is disclosed by the prior art.

The following examples demonstrate preparation of the fluorinated aromatic compounds of low dielectric constants by condensing respective fluorinated aromatic alcohols with acrylyl chloride. Preparation of the fluorinated aromatic alcohols was made in accordance with the prior art procedure disclosed by Griffith and O'Rear.

EXAMPLE 1

This example demonstrates preparation of an etherdiacrylate, a fluorinated phenyl hexafluoropropyl ether of formula I.

The etherdiacrylate was prepared by a modified procedure of the procedure disclosed by Griffith and O'Rear in 1981. Pursuant to the modified procedure, a solution of 7.81 mmol or 0.791 grams of triethylamine in 5 mL of 1,1,2-trichlorotrifluoroethane (Freon® 113) solvent was added dropwise over a period of 10 minutes to a solution of 3.78 mmol or 3.0 grams of the fluorinated phenylether alcohol, shown below, in 10 mL of 1,1,2-trichlorotrifluoroethane solvent maintained in an ice-water bath under nitrogen. The fluorinated phenylether alcohol was prepared by a multistep route reported by Griffith and O'Rear in Polymeric Material Science Engineering, Vol. 53, pp. 766-769 (1985). Thus was formed solution one. After a period of another 10 minute, 7.81 mmol or 0.707 grams of acryloyl chloride in 1,1,2-trichlorotrifluoroethane solvent maintained at room temperature was added drop wise to solution one over a period of 20 minutes. A precipitate formed immediately. After stirring for 2 hours at room temperature, filtration through Celite® filter aid to remove the solid precipitate, followed by evaporation at room temperature in vacuo, 3.2 grams of viscous liquid was obtained.

The viscous liquid was dissolved in a mixture of 20 mL methylene chloride and 10 mL 1,1,2-trichlorotrifluoroethane and filtration through 1 gram neutral alumina gave a clear filtrate. The clear filtrate was then cooled in an ice bath, washed twice with 10 mL 1.3N sodium hydroxide, washed with 10 mL water, dried over anhydrous sodium sulfate, twice percolated and washed through a column of 3 grams of neutral alumina, and evaporated in vacuo at room temperature over a period of 3 hours to give 1.38 grams of a colorless, viscous liquid. The colorless viscous liquid was the fluorinated phenyl hexafluoropropyl ether of formula I. The yield of this compound was 40%. IR, H NMR and C NMR confirmed the structure of this compound. The reaction described above is illustrated as follows:

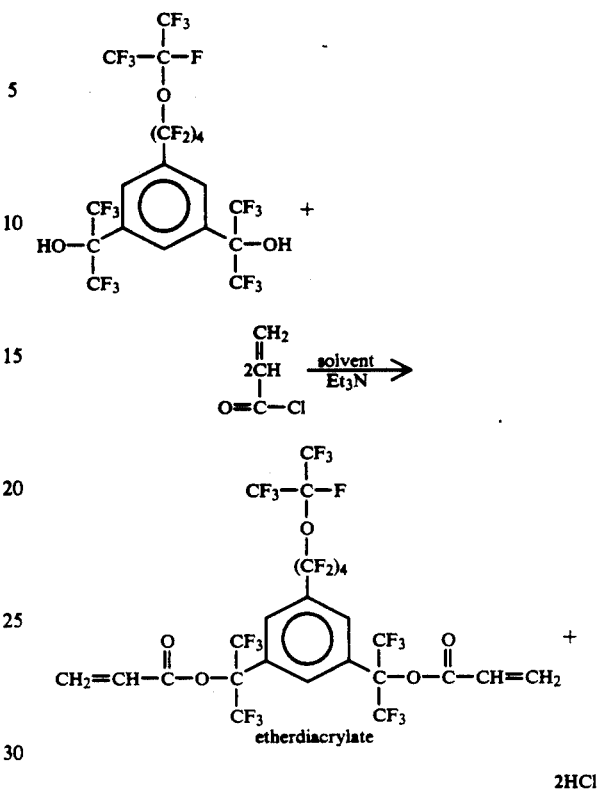

The ether group or oxygen in the etherdiacrylate product is located between the $(CF_2)_4$ group and the $CF(CF_3)_2$ group and is believed to play an important role in the low dielectric constant of the highly fluorinated etherdiacrylates.

EXAMPLE 2

This example demonstrates preparation of a hygroscopic triacrylate, a fluorinated phenyl hexafluoropropyl triacrylate.

The fluorinated phenyl alcohol (triol) was prepared by a multistep procedure disclosed by Soulen and Griffith in Vol. 44 of Journal of Fluorine Chemistry, pp. 203-210 (1989).

The triacrylate was prepared by a procedure similar to that described in connection with preparation of the fluorinated phenyl hexafluoropropyl ether of Ex. 1. Triol in amount of 3.78 m mol or 2.176 grams, triethylamine in amount of 15.0 m mol or 1.517 grams, and acryloyl chloride in amount of 15.0 m mol or 1.358 grams in 1,1,2-trichlorotrifluoroethane were used as in Ex. 1. After filtration and evaporation, 1.82 grams of a viscous liquid was obtained. The viscous liquid was dissolved in a mixture of 20 mL methylene chloride and 20 mL 1,1,2-trichlorotrifluoroethane and a gelatinous solid was removed by filtering through 1 gram of neutral alumina. The filtrate was purified by percolation twice through a column of 3 grams of neutral alumina. Evaporation for 3 hours at room temperature in vacuo gave 1.12 grams of the triacrylate which is a 40% yield. The resulting triacrylate was very viscous, colorless liquid which, upon standing at −13° C., became semisolid. This semisolid, however, was hygroscopic. The reaction described above is illustrated as follows:

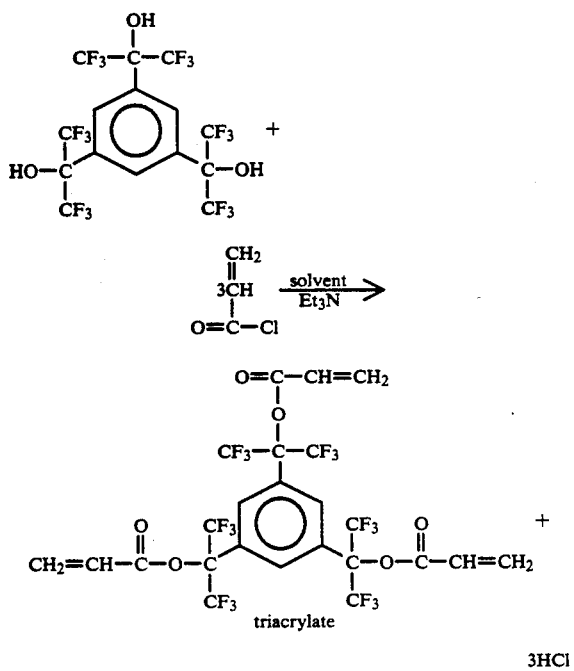

EXAMPLE 3

This example demonstrates preparation of homopolymers from the fluorinated phenyl compounds of Examples 1 and 2 as well as a copolymer of the two compounds, and determination of their dielectric constants.

In order to polymerize the compounds and prepare them for dielectric measurements, liquid etherdiacrylate of Ex. 1 was mixed with a trace amount of azobisisobutyronitrile, a free radical initiator, at room temperature in a first donut model mold made from General Electric Company (GE) RTV 11 silicone molding compound with outer diameter of 7.0 mm, inner diameter of 3.0 mm, and a thickness of 3.0 mm. The semisolid triacrylate of Ex. 2 was mixed with a trace amount of liquid methylethylketone peroxide, a free radical initiator, with some heating to obtain a clear liquid in a second silicone donut model mold. Equal amounts on weight basis of the etherdiacrylate of Ex. 1 and the triacrylate of Ex. 2 were also mixed with a trace amount of methylethylketone peroxide in a third silicone donut model mold.

The fluorinated phenyl compounds of Examples 1 and 2 and a 50/50 weight mixture (respective molar ratio 45/55) of these compounds were polymerized in the donut model molds. This was done by maintaining the molds under inert nitrogen atmosphere while the temperature thereof was raised slowly to 85° C. over a period of 2 hours and then kept at 85°-100° C. for a period of 20 hours. Thermoplastic homopolymer of the fluorinated phenyl compound of Ex. 1 and a thermosetting homopolymer of the compound of Ex. 2 were produced in separate molds, as well as the 50/50 by weight thermosetting copolymer of the compounds of Exs. 1 and 2.

To determine dielectric constants of the two homopolymers and the one copolymer referred to above, a Hewlett Packard 8510 Automated Network Analyzer was used over a frequency band of 500 MHz to 18.5 GHz. The samples were kept at room temperature in air prior to testing for the dielectric constants and measurements were made at room temperature and about 25% relative humidity. Dielectric constant of the homopolymer of the Ex. 1 compound was 2.12, that of the homopolymer of the Ex. 2 compound was 2.23, and that of the copolymer was 2.24. All three of these dielectric constants were determined at 9.5 GHz.

In order to validate the accuracy of the dielectric constant measurements, three samples of virgin poly(tetrafluoroethylene) (Teflon ® plastic) in the same donut mold size were similarly measured and were found to have an average dielectric constant values of 1.96-1.99, which are close to the reported values of 2.0-2.08 for Teflon plastic.

All of the polymers prepared as above described exhibit unusually low dielectric constants over a wide frequency range. The variation of dielectric values over the measured frequency region is within 0.03 for each polymer. Dielectric constant of the copolymer was very close to the homopolymer of the Ex. 2 compound, which indicates that the copolymer apparently was not completely homogeneous and compatible. Since the polymer of the Ex. 1 compound has a lower dielectric constant than the polymer of the Ex. 2 compound and the polymer of Ex. 2 compound has a higher glass transition temperature than the polymer of Ex. 1 compound, the two polymers can be admixed or a copolymer thereof can be prepared to optimize dielectric constant and structural properties of the resultant object. In addition to the lowering effect of the fluorine content, existence of the perfluoroalkyl ether linkage seems to play a very important role in further reducing the dielectric constant values.

What is claimed is:

1. A compound comprising a benzene ring having attached thereto the following groups:

A. Two or more groups having the following structure:

$$R^1-R^2-R^3-$$

where, individually for each of said two or more groups, $R^1$ is a monounsaturated radical of 2 to 6 carbon atoms; $R^2$ is oxygen; and $R^3$ is a fluorinated hydrocarbon radical containing 2 to 6 carbon atoms; and B. at least one group having the following structure:

$$R^4-O-(CX_2)_n-$$

where $R^4$ is a fluorinated hydrocarbon group of 2 to 6 carbon atoms; n is 2 to 6; and X is fluorine.

2. The compound of claim 1 wherein said $R^1$ contains a group selected from the group consisting of acrylic, methacrylic, allylic, halogenated vinyl, vinyl ether, allyl ether, and mixtures thereof; $R^3$ is a saturated perfluorinated hydrocarbon radical; $R^4$ is a perfluorinated hydrocarbon group; and said at least two or more $R^1-R^2-R^3-$ groups are disposed, respectively, on carbons 1 and 3 of said benzene ring and said at least one $R^4-O-(CX_2)_n-$ group is on carbon 5 of said benzene ring.

3. A compound having a dielectric constant below about 2.5 and having the structure:

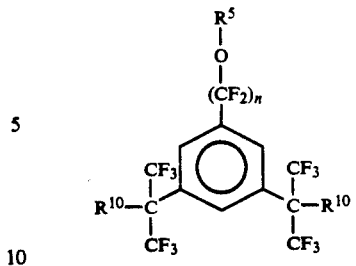

where n is 2 to 6; each $R^{10}$ group is individually selected from the group consisting of acrylate, methacrylate, vinyl ether, allyl ether and lower alkyl ether groups; and $R^5$ is a fluorinated hydrocarbon group of 2 to 6 carbon atoms.

4. The compound of claim 3 having a dielectric constant of less than 2.3, which is liquid or semisolid at room temperature where each $R^{10}$ is selected from the group consisting of acrylate and methacrylate groups, and where $R^5$ is a heptafluoropropyl group.

* * * * *